United States Patent
Actis Goretta et al.

(10) Patent No.: US 10,722,584 B2
(45) Date of Patent: Jul. 28, 2020

(54) INCREASING THE BIOAVAILABILITY OF FLAVAN-3-OLS BY POLYPHENOLS

(71) Applicant: NESTEC S.A., Vevey (CH)

(72) Inventors: Lucas Actis Goretta, Lausanne (CH); Antoine Leveques, Epalinges (CH); Marcia Da Silva Pinto, Lausanne (CH); Magalie Sabatier, Lausanne (CH); Maarit Rein, La Conversion (CH); Gary Williamson, Yorkshire (GB); Fabiola Dionisi, Epalinges (CH)

(73) Assignee: Societe des Produits Nestle S.A., Vevey (CH)

( * ) Notice: Subject to any disclaimer, the term of this patent is extended or adjusted under 35 U.S.C. 154(b) by 0 days.

(21) Appl. No.: 14/646,132

(22) PCT Filed: Nov. 29, 2013

(86) PCT No.: PCT/EP2013/075140
§ 371 (c)(1),
(2) Date: May 20, 2015

(87) PCT Pub. No.: WO2014/083172
PCT Pub. Date: Jun. 5, 2014

(65) Prior Publication Data
US 2015/0313999 A1    Nov. 5, 2015

(30) Foreign Application Priority Data
Nov. 29, 2012 (EP) .................. 12194895

(51) Int. Cl.
| | | |
|---|---|---|
| *A61K 31/35* | (2006.01) | |
| *A61K 47/22* | (2006.01) | |
| *A61K 36/82* | (2006.01) | |
| *A61K 8/49* | (2006.01) | |
| *A61Q 19/00* | (2006.01) | |
| *A61K 31/353* | (2006.01) | |
| *A23L 2/52* | (2006.01) | |
| *A61K 8/97* | (2017.01) | |
| *A61K 31/352* | (2006.01) | |
| *A23K 20/111* | (2016.01) | |
| *A23L 33/105* | (2016.01) | |

(52) U.S. Cl.
CPC ............ *A61K 47/22* (2013.01); *A23K 20/111* (2016.05); *A23L 2/52* (2013.01); *A23L 33/105* (2016.08); *A61K 8/498* (2013.01); *A61K 8/97* (2013.01); *A61K 31/352* (2013.01); *A61K 31/353* (2013.01); *A61K 36/82* (2013.01); *A61Q 19/00* (2013.01); *A23V 2002/00* (2013.01); *A61K 2800/10* (2013.01); *A61K 2800/592* (2013.01); *A61K 2800/92* (2013.01)

(58) Field of Classification Search
None
See application file for complete search history.

(56) References Cited

FOREIGN PATENT DOCUMENTS

| | | | |
|---|---|---|---|
| EP | 2241313 | | 10/2010 |
| EP | 2263481 | | 12/2010 |
| FR | 2899768 | | 10/2007 |
| FR | 2935096 | | 2/2010 |
| JP | 06248267 | * | 9/1994 |
| WO | 9811789 | | 3/1998 |
| WO | WO 0149285 | * | 7/2001 |
| WO | 0234262 | | 5/2002 |
| WO | 02081651 | | 10/2002 |
| WO | 2005004630 | | 1/2005 |
| WO | 2010112510 A1 | | 10/2010 |

OTHER PUBLICATIONS

Merck Manual, Fifteenth Editiion, pp. 2246-2260, 2497-2503.*
Lambert et al. "Effect of genistein on the bioavailability and intestinal cancer chemopreventive activity of (−)-epigallocatechine-gallate" Carcinogenesis, 2008, vol. 29, No. 10, pp. 2019-2024.
Office Action issued in corresponding Japanese Patent Application No. 2015-544486 dated Sep. 12, 2017 and English Translation of same.
Van Zanden, J.J., et al., "Quantitative structure activity relationship studies on the flavonoid mediated inhibition of multidrug resistance proteins 1 and 2", Biochem. Pharmacal., 2005, vol. 69, pp. 699-708.
Nguyen, H., et al., "Effects of flavonoids on MRP1-mediated transport in Panc-1 cells", J. Pharm. Sci., 2003, vol. 92, pp. 250-257.
Office Action issued in corresponding Chinese Patent Application No. 201380061853.X dated Mar. 17, 2017 and English Translation of same.

* cited by examiner

*Primary Examiner* — Shobha Kantamneni
(74) *Attorney, Agent, or Firm* — K&L Gates LLP

(57) ABSTRACT

The present invention relates generally to the field of flavan-3-ols. In particular, the present invention provides a way to increase the bioavailability of flavan-3-ols. Embodiments of the present invention relate to the use of at least one polyphenolic compound in a composition comprising at least one flavan-3-ol for increasing the bioavailability of said flavan-3-ol, wherein the at least one polyphenolic compound is selected from a group consisting of flavonols, flavones, isoflavones, flavanones, or combinations thereof.

11 Claims, 5 Drawing Sheets

A

B

R1 = H, O, OH or not R5
R2 = H, OH or not R5
R3 = H or O
R4 = H. O. or OCH3

R5

C

R3 = H or O
R4 = H. O. or OCH3

| Treatment | AUC (µg/mL*min) |
|---|---|
| GT (control) | 40 ± 12 |
| GTHG | 50 ± 18 |
| Relative difference | + 25% |

FIG. 5

INCREASING THE BIOAVAILABILITY OF FLAVAN-3-OLS BY POLYPHENOLS

CROSS REFERENCE TO RELATED APPLICATIONS

The present application is a National Stage of International Application No. PCT/EP2013/075140, filed on Nov. 29, 2013, which claims priority to European Patent Application No. 12194895.4, filed on Nov. 29, 2012, the entire contents of which are being incorporated herein by reference.

The present invention relates generally to the field of flavan-3-ols. In particular, the present invention provides a way to increase the bioavailability of flavan-3-ols. Embodiments of the present invention relate to the use of at least one polyphenolic compound in a composition comprising at least one flavan-3-ol for increasing the bioavailability of said flavan-3-ol, wherein the at least one polyphenolic compound is selected from a group consisting of flavonols, flavones, isoflavones, flavanones, or combinations thereof.

Flavan-3-ols (including for example "catechins") are present in several food sources such as cocoa, tea and apples. Several epidemiological, in vitro and in vivo studies have associated the presence of these compounds to health promoting effects such as antioxidative and anti-inflammatory benefits (Aron, P. M., et al., 2008, Molecular Nutrition & Food Research 52, 79-104).

In general flavan-3-ols are subjected to several phase II enzymes leading to conjugation with methyl groups (catechol-O-methyltransferases—COMT), sulfate groups (sulphotransferases—SULT) and glucuronyl groups (uridine-5'-diphosphate glucuronosyl-transferases—UDPGT). However, EGCG, the main flavan-3-ol present in green tea, has been reported to be present in human plasma mainly in its native form (Williamson et al., 2011, Mol Nutr Food Res 55, 864-873).

The oral bioavailability of, e.g., the green tea flavan-3-ols is low, resulting in systemic flavan-3-ols levels in humans which are many fold lower than the effective concentrations determined in in vitro systems (Lambert et al., 2007, Mol. Pharmaceutics 4, 819-825). Many approaches to increase bioavailability of flavan-3-ols from green tea have been reported in literature such as the administration of tea in combination with piperine, an alkaloid present in black pepper, and peracetylation of EGCG. Another strategy to improve the absorption of flavan-3-ols is the administration during a fasting state, however, it is important to notice that some human studies have shown that high doses of green tea preparations can be potentially toxic (Chow et al., 2005, Clinical Cancer Research 11, 4627-4633; Bonkovsky, 2006, Ann Intern Med 144, 68-71).

Hence there is a need in the art for alternative ways to improve the absorption of flavan-3-ols while avoiding overdosing of flavan-3-ols.

Any reference to prior art documents in this specification is not to be considered an admission that such prior art is widely known or forms part of the common general knowledge in the field.

The object of the present invention was it therefore to improve the state of the art and in particular to provide a way to administer flavan-3-ols while ensuring effective absorption and a high bioavailability, or to at least to provide a useful alternative to what is known in the art.

The inventors were surprised to see that the object of the present invention could be achieved by the subject matter of the independent claims. The dependent claims further develop the idea of the present invention.

Accordingly, the present invention provides a new approach for increasing the absorption of the flavan-3-ols, in particular their biologically active forms, parent compounds and/or metabolites. In accordance with the present invention this is achieved by co-administration of these compounds with polyphenols, e.g., dietary polyphenols.

As used in this specification, the words "comprises", "comprising", and similar words, are not to be interpreted in an exclusive or exhaustive sense. In other words, they are intended to mean "including, but not limited to".

The present inventors have conducted extensive in vitro experiments using a Caco-2 cell model and in vivo human bioavailability study that could show that the co-administration of flavan-3-ols with certain polyphenols can increase the absorption of flavan-3-ols and/or their metabolites. Without wishing to be bound by theory the inventors currently believe that the absorption of flavan-3-ols is modulated by the presence of other polyphenols through several mechanisms, for example through competition with metabolizing enzymes and/or through the inhibition of the efflux of flavan-3-ol and/or their metabolites from the cells.

Consequently, the invention relates in part to a non-therapeutic use of at least one polyphenolic compound in a composition comprising at least one flavan-3-ol for increasing the bioavailability of said flavan-3-ol, wherein the at least one polyphenolic compound is selected from a group consisting of flavonols, flavones, isoflavones, flavanones, or combinations thereof.

In a further aspect, the invention relates to a composition comprising at least one polyphenolic compound selected from a group consisting of flavonols, flavones, isoflavones, flavanones, or combinations thereof and at least one flavan-3-ol for use in the treatment or prevention of disorders that can be treated or prevented by flavan-3-ol administration.

BRIEF DESCRIPTION OF THE FIGURES

FIG. 5 shows the kinetic parameters such as AUC (area under the curve) and $C_{max}$ (maximum concentration) for EGCG (Epigallocatechin 3-gallate) from subjects in the control (GT=green tea extract) and treatment groups (GT + HG=green tea extract + hesperitin 7-glucoside).

Figure 1:
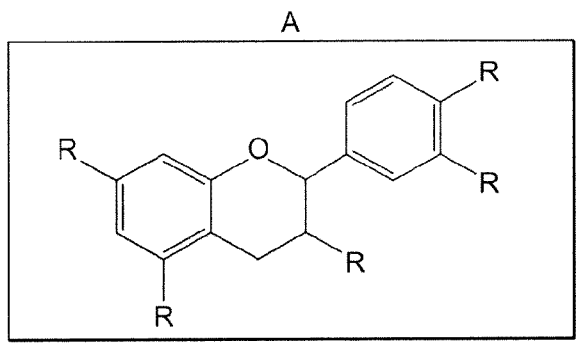
FIG. 1 shows the general formulas (A, B and C) of compounds that may form a mixture in accordance with this invention.
Figure 1:
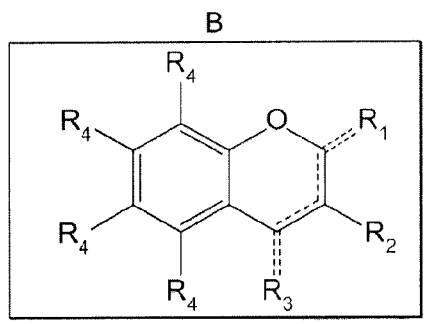
Figure 1:
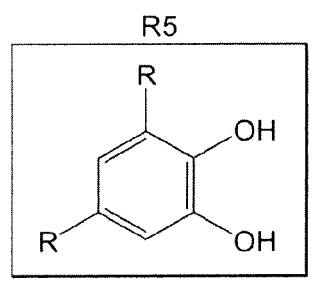
Figure 1:
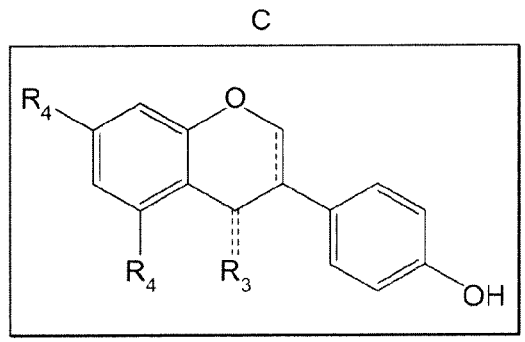

Table 1 presents the kinetic parameters such as AUC (area under the curve) and $C_{max}$ (maximum concentration) for EGCG (Epigallocatechin 3-gallate) from subjects in the control (GT=green tea extract) and treatment groups (GT+HG=green tea extract+hesperitin 7-glucoside).

Consequently the present invention relates in part to a non-therapeutic use of at least one polyphenolic compound in a composition comprising at least one flavan-3-ol for increasing the bioavailability of said flavan-3-ol.

Bioavailability may be defined as the proportion of the administered substance capable of being absorbed and available for use or storage.

The present invention also relates to a composition comprising at least one flavan-3-ol for use in the treatment or prevention of disorders that can be treated or prevented by flavan-3-ol administration, wherein the composition further comprises at least one polyphenolic compound for increasing the bioavailability of said flavan-3-ol.

The present invention further relates to the use of at least one flavan-3-ol for the preparation of a composition for treating or preventing disorders that can be treated or prevented by flavan-3-ol administration, wherein the composition further comprises at least one polyphenolic compound for increasing the bioavailability of said flavan-3-ol.

Disorders that can be treated or prevented by flavan-3-ol administration are well known to skilled artesians. Examples of disorders that can be treated or prevented by flavan-3-ol administration may be selected from the group consisting of cardiovascular diseases, type 2 diabetes, overweight, obesity, inflammatory disorders, cognitive impairment and oxidative skin damage.

The inventors have used a Caco-2 cell model to study, how the flavan-3-ol absorption is influenced, if the flavan-3-ols are co-administered with other polyphenols.

The inventors found that the absorption of flavan-3-ols could be significantly enhanced if the flavan-3-ols were co-administered with flavonols, flavones, isoflavones, and/or flavanones, while other tested polyphenols had no significant effect on flavan-3-ol absorption.

The inventors also conducted a human bioavailability study in order to evaluate in vivo how the flavan-3-ol absorption, more specifically EGCG, is influenced, if the flavan-3-ols are co-administered with other polyphenols.

The inventors found that the absorption of EGCG could be significantly enhanced if the flavan-3-ols were co-administered with for example flavanones such as hesperitin 7-glucoside.

Hence, in accordance with the present invention, the at least one polyphenolic compound may be selected from a group consisting of flavonols, flavones, isoflavones, flavanones, or combinations thereof.

This increase in absorption clearly demonstrates an improved bioavailability of flavan-3-ols if co-administered with the tested polyphenols.

Through improving bioavailability of flavan-3-ols by co-administration with polyphenols the capacity for a beneficial change or a therapeutic effect of such a flavan-3-ol intervention is improved.

Consequently, the co-administration of flavan-3-ols with polyphenols in accordance with the present invention allows it to increase the bioefficacy of said flavan-3-ol.

Compounds falling within general formula (I) as defined hereinbelow are particularly effective at enhancing the absorption of flavan-3-ols.

In an embodiment the at least one polyphenolic compound is a flavonol, flavone, isoflavone, and/or flavanone of formula (I)

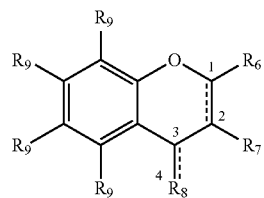
(I)

Wherein
$R_6$ is selected from the group consisting of: H, OH, $OCH_3$ and, a cycloalky of formula (II)

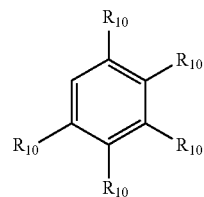
(II)

$R_7$ is selected from the group consisting of: H, OH, $OCH_3$ and, a cycloalky of formula (II);
$R_8$ is selected from the group consisting of: H, O, OH and, $OCH_3$;
each $R_9$ substituent is independently selected from the group consisting of: H, OH and, $OCH_3$;
each $R_{10}$ of formula (II) is independently selected from the group consisting of: H, OH and, $OCH_3$;
and
the dotted lines between positions 1 and 2, and 3 and 4 in formula (I) represent optional double bonds;
with the provisos that
if $R_6, R_7$, or $R_8$ is OH then any adjacent $R_6, R_7$, or $R_8$ substituent is not OH;
if one $R_9$ substituent is OH then any adjacent $R_9$ substituent is not OH;
when $R_8$ is O there is a double bond between positions 3 and 4;
and
if one $R_{10}$ substituent of formula (II) is OH then any adjacent $R_{10}$ substituent of formula (II) is not OH.

In an embodiment the composition comprises a flavonol, flavone, isoflavone, and/or flavanone of formula (I) selected from the group consisting of:
3-hydroxyflavone, Kaempferide, Kaempferol, Isorhamnetin, Natsudaidain, Pachypodol, Rhamnazin, Flavone, Apigenin, Chrysine, Hesperitin, Naringinine, Sakuranetin, genistein, equol, nevadensin, or combinations thereof.

In an embodiment the composition comprises a flavonol, flavone, isoflavone, and/or flavanone selected from the group consisting of: isorhamnetin, kaempferol, diosmetin, nevadensin, chrysin, equol, genistein, hesperitin, or combinations thereof.

In an embodiment the at least one polyphenolic compound is a flavonol, flavone, isoflavone, and/or flavanone of formula (I) as defined hereinabove, wherein the isoflavone is an isoflavandiol.

In a particular embodiment the at least one polyphenolic compound is a flavone, isoflavone and/or flavanone of formula (I) as defined hereinabove, wherein the isoflavone is an isoflavandiol.

In an embodiment the at least one polyphenolic compound is a flavone and/or flavanone of formula (I) as defined hereinabove.

In an embodiment the at least one polyphenolic compound is a flavone and/or flavanone selected from the group consisting of: isorhamnetin, kaempfernol, diosmetin, nevadensin, chrysin, hesperitin, or combinations thereof.

A non-therapeutic use may be a cosmetic use, for example.

It is preferred if the at least one polyphenolic compound is obtained from natural sources, for example from dietary sources.

A wide variety of fruits and vegetables may be used as source of flavonols. Typically, the daily intake of flavonols is in the range of 20-50 mg per day for flavonols.

Cereals and herbs are typical sources of flavones. Typically, the daily intake of flavones is in the range 20-50 mg per day for flavones.

Soy is a good natural source of isoflavones and so are several members of the Leguminosae plant family. Further dietary sources are chick peas, alfalfa, and peanuts.

Flavanones are typically found in citrus fruits, such as oranges, grapefruit, lemons, and limes, for example. They are also found in ingredients frequently used in the kitchen, such as parsley, celery, and certain hot peppers.

Hence, the polyphenolic compounds used in the framework of the present invention may be provided as pure compounds, but also as extracts from dietary ingredients, or directly as processed or un-processed dietary ingredient.

Providing the polyphenolic compounds from such well known natural sources has the advantage, that the compounds are well-accepted by consumers, are generally considered as safe in reasonable amounts and the natural source can even be used to enrich food products in terms of taste and variety.

For example, the at least one polyphenolic compound may selected from the group consisting of isorhamnetin, kaempferol, diosmetin, nevadensin, chrysin, equol, genistein, hesperitin, or combinations thereof.

Isorhamnetin and kaempferol are flavonols; diosmetin, nevadensin, chrysin are flavones; equol and genistein are isoflavones and hesperitin is a flavanone.

The flavan-3-ols may also be provided from natural sources. They may be provided as extracts from these natural sources or as the natural source itself as food ingredient, processed or unprocessed.

For example, the flavan-3-ols may originate from green tea, white tea, wild plant fruits, in particular berries, apples, cocoa beans or other fruits containing flavan-3-ols.

Green tea, the most commonly consumed beverage in the world after water, is a very good source of flavan-3-ols. Although amounts of flavan-3-ols present in green tea vary depending on factors influencing plant metabolism such as light, rain fall, temperature, nutrient availability, leaf age, and genetic make-up, they usually constitute 16-24% of the dry matter of fresh green tea leaves. As flavan-3-ols are typically stable during the manufacturing of green tea, they represent a major part of commercial green tea extracts.

The major green tea flavan-3-ols are catechins, i.e. (+)-catechin (C) and its stereoisomer and four derivatives, namely (−)-epicatechin (EC), (−)-epigallocatechin (EGC), (−)-epigallocatechin-3-gallate (EGCg), (−)-epicatechin-3-gallate (ECg).

Flavan-3-ols display several health benefits that are often associated with their antioxidant activities including scavenging of reactive oxygen and nitrogen species, free metal chelation, inhibition of transcriptional factors and inhibition of oxidative enzymes such as lipoxygenase and cycloxygenase.

In one embodiment, the flavan-3-ols are from green tea. Other sources of flavan-3-ols may alternatively be used.

Green tea or other plant sources may be used in the form of fresh, concentrated or dried materials, for example, air or freeze dried material.

For example, the flavan-3-ols used in the present invention may be selected from the group consisting of (+)-catechin (C), (−)-epicatechin (EC), gallocatechin (GC), gallocatechin gallate (GCG), (−)-epigallocatechin (EGC), (−)-epigallocatechin-3-gallate (EGCg), (−)-epicatechin-3-gallate (ECg), or combinations thereof.

In an embodiment the flavan-3-ols used in the present invention is (−)-epicatechin.

In an embodiment the flavan-3-ols used in the present invention is (−)-epicatechin-3-gallate.

The amount of flavan-3-ols in the composition will depend on its intended application.

In therapeutic applications, active compounds are administered in an amount sufficient to at least partially cure or arrest the symptoms of a disorder and/or its complications. An amount adequate to accomplish this is defined as "a therapeutic effective dose". Amounts effective for this purpose will depend on a number of factors known to those of skill in the art such as the severity of the disorder and the weight and general state of the patient.

In prophylactic applications, active compounds according to the invention are administered to a patient susceptible to or otherwise at risk of a particular disorder in an amount that is sufficient to at least partially reduce the risk of developing a disorder. Such an amount is defined to be "a prophylactic effective dose". Again, the precise amounts depend on a number of patient specific factors such as the patient's state of health and weight.

In non-therapeutic, e.g., cosmetic applications, active compounds according to the invention are administered to a person in an amount sufficient to at least partially reduce a visible or tangible imperfection of a physical appearance of a person. Such an amount is defined to be "a cosmetic effective dose". Again, the precise amounts depend on a number of person specific factors such as the persons gender, race, complexion, age, or state of health.

In the framework of the present invention, the active compounds may be administered in a prophylactic effective dose, a therapeutic effective dose, or in a cosmetic effective dose.

The active compounds used in the present invention are flavan-3-ols.

For example, the flavan-3-ols may be present in the composition described in the present invention in an amount corresponding to 0.5-50 weight-% of the dry weight of the composition, for example 1.5-20 weight-% of the dry weight of the composition, or 2-10 weight-% of the dry weight of the composition.

In order to improve absorption and bioavailability of the flavan-3-ols optimally, an appropriate ratio of polyphenolic compounds and flavan-3-ols should be used.

This ideal ratio will depend on many factors, such as the nature of the food matrix, the concentration of the active compound and the details of storage and consumption, for example. Skilled artesians will be able to identify such optimal ratios. For example, the compositions of the present invention may contain polyphenolic compounds and flavan-3-ols in a weight ratio in the range of 1:1 to 100:1, for example in a weight ratio in the range of 5:1 to 75:1, in a weight ratio in the range of 10:1 to 50:1, or in a weight ratio in the range of 15:1 to 25:1.

The composition of the present invention may be to be administered orally or it may be applied to the body surface, for example. The composition may be a foodstuff, a drink, a food supplement, a pet food product, a nutritional, or a cosmetic composition.

A food composition for human consumption may be a nutritional complete formula, a dairy product, a chilled or shelf stable beverage, a mineral or purified water, a liquid drink, a soup, a dietary supplement, a meal replacement, a nutritional bar, a confectionery, a milk or a fermented milk product, a yoghurt, a milk based powder, an enteral nutrition product, an infant formula, an infant nutritional product, a cereal product or a fermented cereal based product, an ice-cream, a chocolate, coffee, a culinary product such as mayonnaise, tomato puree or salad dressings or a pet food.

For ingestion, many embodiments of oral compositions and in particular of food supplements are possible. They may be formulated as sugar-coated tablets, pills, pastes, gums, gelatine capsules, gels, emulsions, tablets, capsules or drinkable solutions or emulsions, which can then be taken directly with water or by any other known means.

The food composition or food supplement may also include a sweetener, a stabilizer, an antioxidant, an additive, a flavouring or a colorant. The composition may also contain synthetic or natural bioactive ingredients such as amino acids, fatty acids, vitamins, minerals, carotenoids, polyphenols, etc. that can be added either by dry or by wet mixing to said composition before pasteurization and/or drying.

According to an embodiment, the composition of the invention may be used cosmetically. By "cosmetic use" is meant a non-therapeutic use which may improve the aesthetic aspect or comfort of the skin, coat and/or hair of humans or pets.

When used cosmetically, the composition of the invention may assume any form of food composition or supplement described above. Preferably, it is in the form of dietary supplements, which may be in liquid or dry form, such as solutions, sprays, tablets, capsules, gelatine capsules, lozenges, powders, gels, emulsions etc. More preferably it is in the form of a capsule. A supplement for cosmetic purpose can additionally comprise a compound active with respect to the skin.

The invention also relates to topical compositions. Such topical compositions may be formulated as lotions, shampoos, creams, sun-screens, after-sun creams, anti-ageing creams and/or ointments, for example. A composition which can be used topically may additionally comprises a fat or an oil which can be used in cosmetics, for example those mentioned in the CTFA work, Cosmetic Ingredients Handbook, Washington. It is also possible to add other cosmetically active ingredients. Such compositions may additionally comprise a structuring agent and/or an emulsifier. Other excipients, colorants, fragrances or opacifiers can also be added to the composition. It will be appreciated that cosmetic products may contain a mixture of different ingredients known to the skilled person, ensuring a fast penetration of the said substance into the skin and preventing degradation thereof during storage.

It will be understood that the concept of the present invention may likewise be applied as an adjuvant therapy assisting in presently used medications.

Those skilled in the art will understand that they can freely combine all features of the present invention disclosed herein. In particular, features described for the non-therapeutic use of the present invention may be combined with the composition for use of the present invention and vice versa. Further, features described for different embodiments of the present invention may be combined.

Although the invention has been described by way of example, it should be appreciated that variations and modifications may be made without departing from the scope of the invention as defined in the claims.

Furthermore, where known equivalents exist to specific features, such equivalents are incorporated as if specifically referred in this specification. Further advantages and features of the present invention are apparent from the figures and non-limiting examples.

EXAMPLE 1

In Vitro Caco 2-Cell Model

Method: Caco-2 human epithelial colorectal adenocarcinoma cells were used to investigate the transport of (−)-epicatechin in vitro.

Cells were grown in high glucose DMEM supplemented with 20% heat inactivated fetal bovine serum, non-essential amino acids and 2 mM L-glutamine, amphotericin B (1 µg/ml), penicillin (100 U/ml), and streptomycin (100 µg/ml) and maintained at 37° C. and 5% $CO_2$. The medium was replaced every 2 days and the cells were reseeded every 7 days. Then, cells were seeded in 12-well transwell inserts at a density of 20,000 cells per $cm^2$ and the medium on both sides was replaced every 2 days. After 21 days, cells were already differentiated.

On the experiment day, medium was removed and replaced by HBSS supplemented with 25 mM glucose, 10 mM HEPES and 1.8 mM $CaCl_2$. Catalase (189 U/ml) and ascorbic acid (0.5 mM) were added to prevent oxidation of the test compounds. Then, (−)-epicatechin (100 µM) alone or plus other polyphenols (2 to 100 µM) were placed in the apical side of the cell monolayers and incubated for 2 h. All compounds were added to the exposure medium from stock solutions in DMSO. The concentration of DMSO at the apical side was kept at 0.05% in each experiment. Conjugated compounds (metabolites) were detected in the cell culture media using ultra-performance liquid chromatography using an Acquity UPLC HSS C18 2.1×100 mm, 1.8 µm column (Waters, Switzerland) equipped with HSS C18 VanGuard pre-column (Waters, Switzerland).

Results: Since (−)-epicatechin is present in plasma as conjugates (metabolites), these compounds will be the compounds circulating in blood and most likely reaching the different sites of action and exerting the beneficial effects reported in literature.

Figure 2:
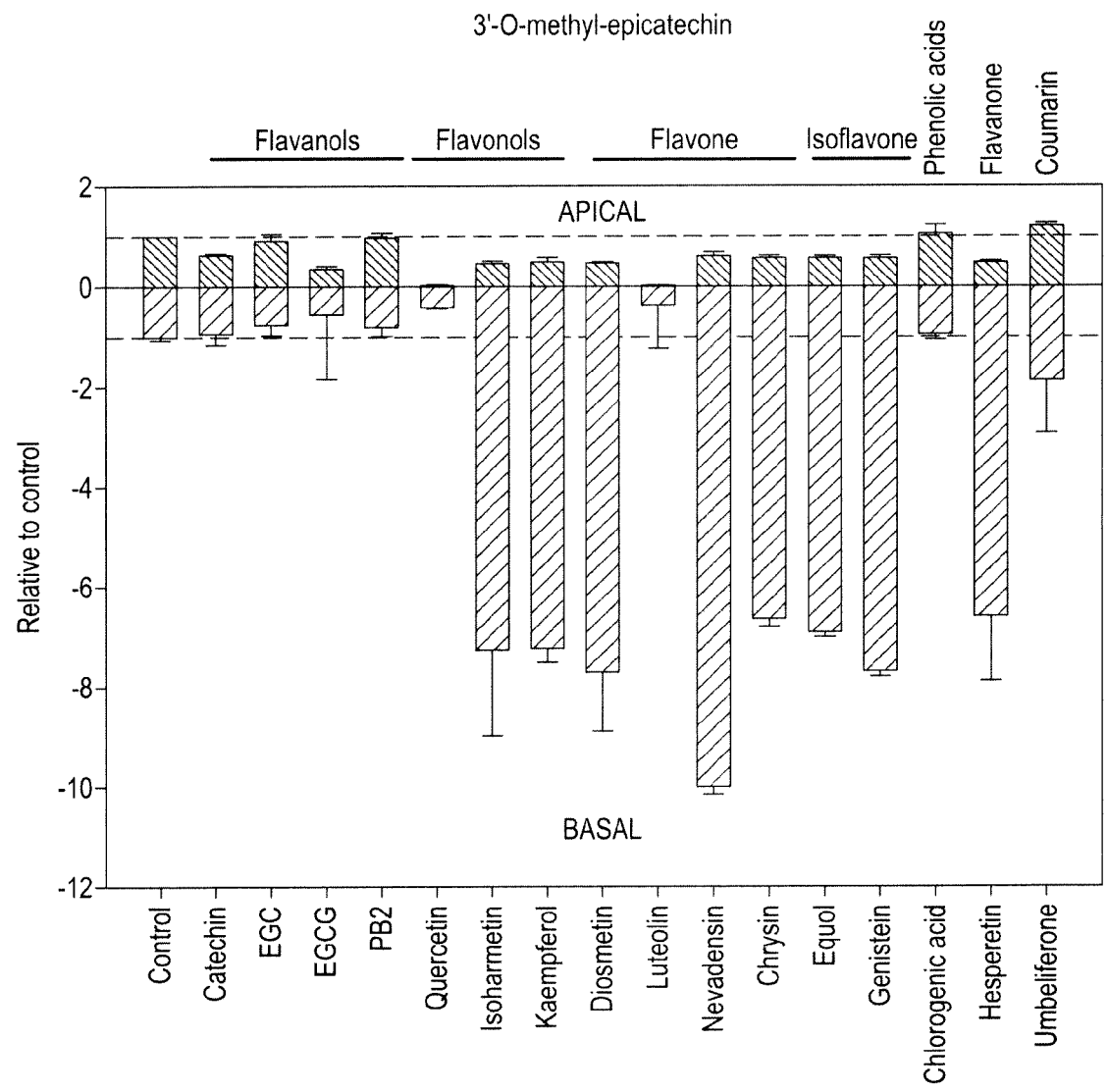
FIG. 2 shows the effect co-incubation of different polyphenolic compounds with (−)-epicatechin on the apical efflux and basolateral transport of (−)-3'-O-methyl-(−)-epicatechin.
Figure 3:
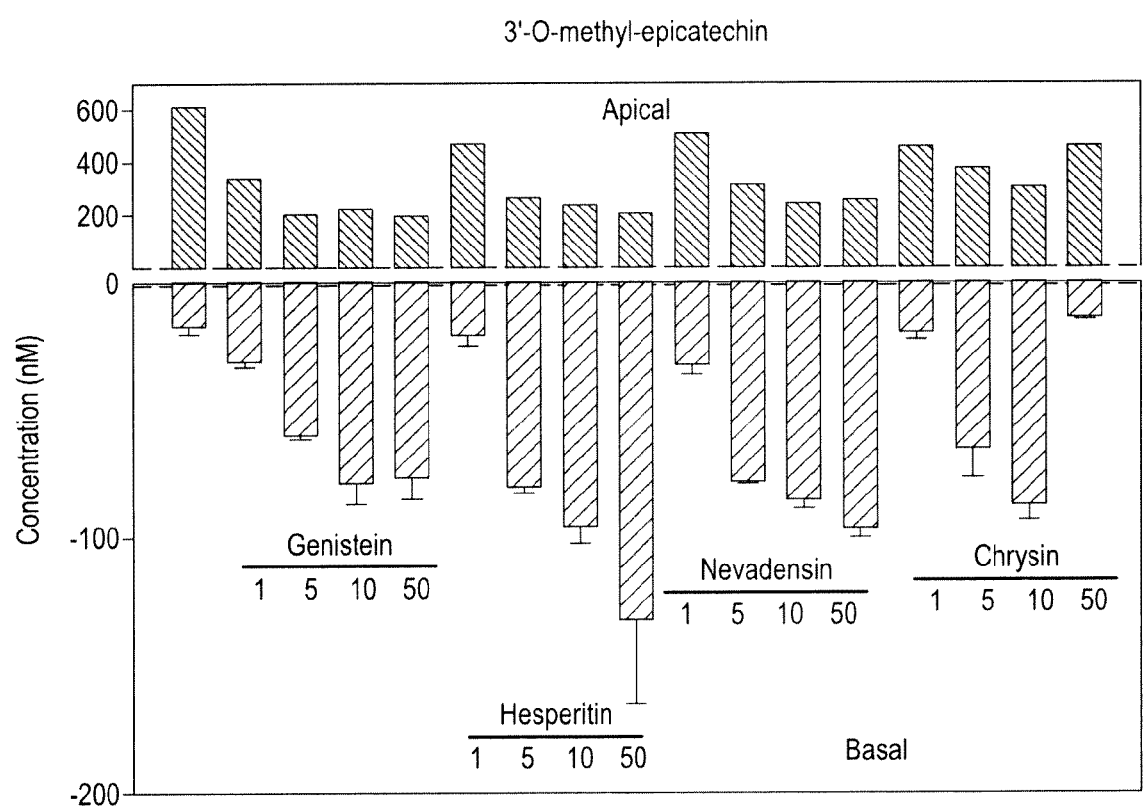
FIG. 3 shows the dose-dependent effect of co-incubation of genistein, nevadensin, hesperitin and chrysin with (−)-epicatechin on apical efflux and basolateral transport of 3'-O-methyl-epicatechin (metabolite).

The results obtained from this in vitro model showed that, when in combination with some selected polyphenols, there was a significant increase in the concentration of methyl and/or sulfate epicatechin metabolites in the basal compartment (FIGS. 2 and 3), indicating that these metabolites were better absorbed.

Figure 4:
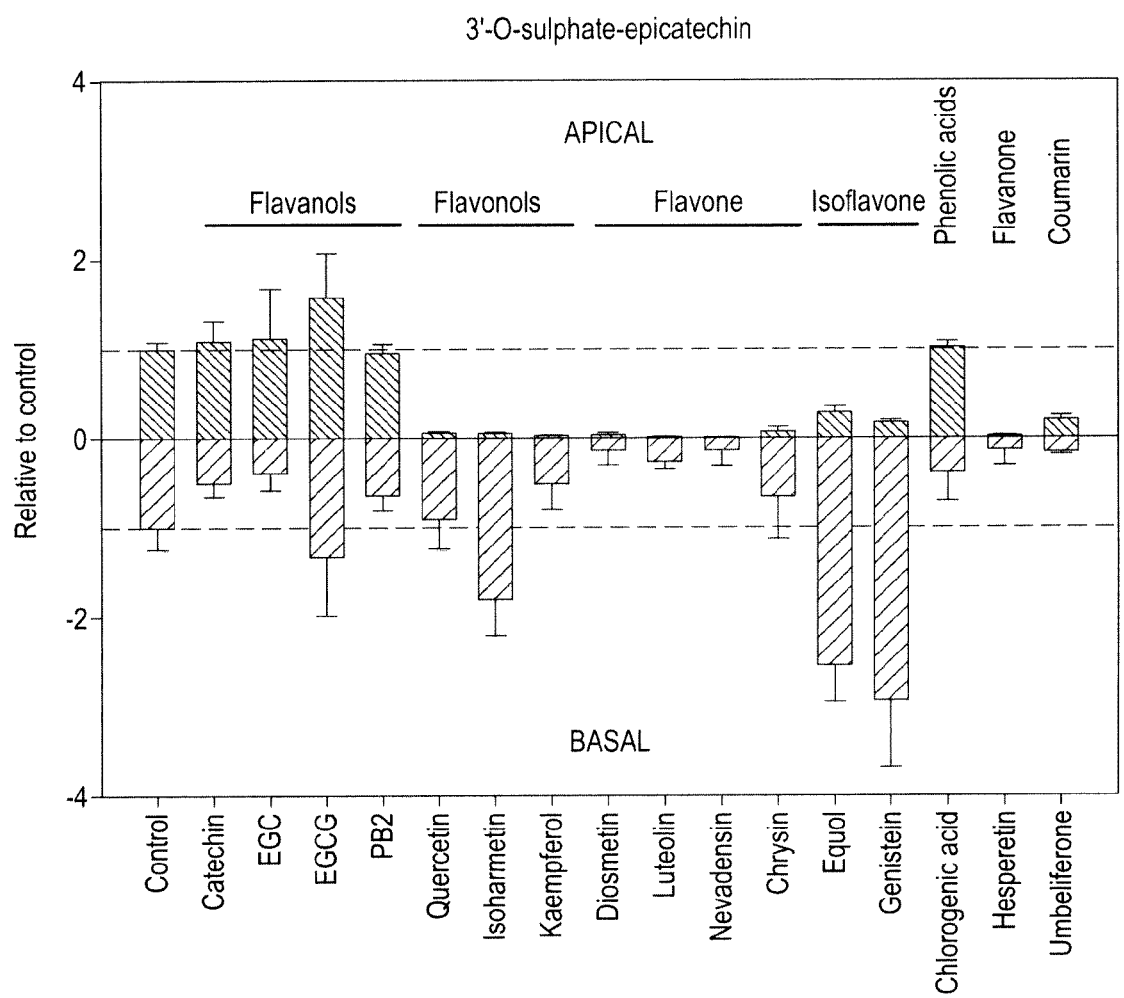
FIG. 4 shows the effect of co-incubation of different polyphenolic compounds with (−)-epicatechin on the on the apical efflux and basolateral transport of 3'-O-sulfate-epicatechin (metabolite).

In addition, a dose-dependent effect of the co-incubation of selected polyphenols with (−)-epicatechin was observed (FIG. 4).

EXAMPLE 2

In Vivo Human Bioavailability Intervention Study

Method: 12 healthy male (20-50 yrs) were enrolled in a randomized and double blind crossover design of four treatments with a minimum of 1 week wash-out period between each treatment was applied.

In the present invention, only 2 treatments are object of investigation: green tea extract (control) and green tea extract+hesperitin 7-glucoside (intervention).

Each treatment was formulated to contain 1 g equivalent of Choladi green tea extract. Subjects in the intervention group received a mixture of 1 g of green tea extract and 100 mg of hesperitin-7-glucoside.

After ingestion, plasma was collected over 24 h. Plasma EGCG analyses were performed by HPLC coupled with an electrochemical detection.

EGCG bioavailability was calculated from plasma kinetics by measuring the Area Under its concentration-time Curve (AUC).

Results: contrary to (−)-epicatechin, EGCG is present in plasma mainly as its native form (parent compound), meaning that the parent compound will be most likely the compound reaching the different sites of action and exerting the beneficial effects reported in literature.

The results showed that EGCG from green tea extract was well absorbed when compared to published data. However, the AUC of EGCG in green tea formulation with hesperitin 7-glucoside was approximately 25% higher than the control (green tea extract) (Table 1).

The results from this bioavailability study showed that, when in combination with some selected polyphenols such as hesperitin 7-glucoside, there was a significant increase in the concentration of plasma EGCG, indicating that this compound was better absorbed.

The invention claimed is:

1. A method of increasing the bioavailability of (−)-epicatechin (EC), the method comprising:
administering to an individual a composition comprising nevadensin and the (−)-epicatechin (EC), the composition contains the nevadensin and the (−)-epicatechin (EC) in a weight ratio of 15:1 to 25:1.

2. The method of claim 1, wherein the nevadensin is obtained from natural sources.

3. The method of claim 1 wherein the (−)-epicatechin (EC) originates from at least one source selected from the group consisting of green tea, wild plant fruits, apples, cocoa beans and other fruits containing (−)-epicatechin (EC).

4. The method of claim 1 wherein the composition is a form selected from the group consisting of a foodstuff, a drink, a food supplement, a pet food product, a nutritional, and cosmetic composition.

5. The method of claim 1 wherein the composition further comprises at least one component selected from the group consisting of a stabilizer, a flavoring ingredient and a colorant.

6. The method of claim 1 wherein the composition is administered orally.

7. The method of claim 1 wherein the bioefficacy of the (−)-epicatechin (EC) is increased by the nevadensin.

8. The method of claim 1 wherein the (−)-epicatechin (EC) is 2-6.25% of the composition by dry weight.

9. The method of claim 1 wherein the (−)-epicatechin (EC) is 0.5-6.25% of the composition by dry weight.

10. The method of claim 1 wherein the (−)-epicatechin (EC) is 1.5-6.25% of the composition by dry weight.

11. The method of claim 1 wherein the nevadensin and the (−)-epicatechin (EC) are the only polyphenolic compounds in the composition.

* * * * *

UNITED STATES PATENT AND TRADEMARK OFFICE
CERTIFICATE OF CORRECTION

| | |
|---|---|
| PATENT NO. | : 10,722,584 B2 |
| APPLICATION NO. | : 14/646132 |
| DATED | : July 28, 2020 |
| INVENTOR(S) | : Lucas Actis Goretta et al. |

It is certified that error appears in the above-identified patent and that said Letters Patent is hereby corrected as shown below:

On the Title Page

Item (72) Change the name of Gary Williamson to "Gray Williamson".

Signed and Sealed this
Seventh Day of February, 2023

Katherine Kelly Vidal
Director of the United States Patent and Trademark Office